(12) United States Patent
Burns, Jr. et al.

(10) Patent No.: US 8,393,321 B2
(45) Date of Patent: Mar. 12, 2013

(54) DRUG DELIVERY SYSTEM FOR CONSCIOUS SEDATION

(75) Inventors: William H. Burns, Jr., Orchard Park, NY (US); John C. McNeirney, Fairburn, GA (US); Ross C. Terrell, Phillipsburg, NJ (US)

(73) Assignee: Piramal Critical Care, Inc., Orchard Park, NY (US)

( * ) Notice: Subject to any disclaimer, the term of this patent is extended or adjusted under 35 U.S.C. 154(b) by 0 days.

(21) Appl. No.: 10/272,794

(22) Filed: Oct. 17, 2002

(65) Prior Publication Data

US 2003/0233086 A1 Dec. 18, 2003

Related U.S. Application Data

(60) Provisional application No. 60/330,063, filed on Oct. 17, 2001.

(51) Int. Cl.
*A61M 16/00* (2006.01)

(52) U.S. Cl. ............... 128/203.11; 604/24; 128/205.11

(58) Field of Classification Search ............... 604/23, 604/24; 128/204.18, 204.22, 205.11, 203.12, 128/203.13
See application file for complete search history.

(56) References Cited

U.S. PATENT DOCUMENTS

| | | | |
|---|---|---|---|
| 2,549,593 A | 3/1951 | Gardnier | |
| 3,183,906 A | 5/1965 | Moyat | |
| 3,251,361 A | 5/1966 | Rusz | |
| 3,531,463 A | 9/1970 | Gustafson | |
| 3,592,191 A | 7/1971 | Jackson | |
| 3,627,708 A | 12/1971 | Morse et al. | |
| 3,665,073 A | 5/1972 | Marshall et al. | |
| 3,843,566 A | 10/1974 | Barrett | |
| 4,015,599 A * | 4/1977 | Peterson | 128/204.13 |
| 4,587,966 A | 5/1986 | Albarda | |
| 4,686,975 A * | 8/1987 | Naimon et al. | 128/204.23 |
| 4,770,168 A * | 9/1988 | Rusz et al. | 128/203.12 |
| 4,927,766 A | 5/1990 | Auerbach et al. | |
| 5,228,434 A * | 7/1993 | Fishman | 128/203.12 |
| 5,237,990 A * | 8/1993 | Psaros et al. | 128/204.21 |
| 5,423,313 A | 6/1995 | Olsson et al. | |
| 5,505,236 A | 4/1996 | Grabenkort et al. | |
| 5,546,931 A | 8/1996 | Rusz | |
| 5,718,223 A * | 2/1998 | Protas et al. | 128/204.21 |

(Continued)

FOREIGN PATENT DOCUMENTS

| | | |
|---|---|---|
| DE | 4105972 | 8/1992 |
| EP | 0106015 | 4/1984 |

(Continued)

OTHER PUBLICATIONS

Abboud, T.K. MD, et al. Enflurane Analgesia in Obstetrics, Anesthesia and Analgesia, Mar. 1981, vol. 60, No. 3, pp. 133-137.

(Continued)

*Primary Examiner* — Laura Bouchelle
(74) *Attorney, Agent, or Firm* — Hodgson Russ LLP (57) ABSTRACT

Inhalant anesthetics are developed with a number of properties including rapid onset and recovery, controllability, and, ideally, a broad safety profile. The efficacy of these agents is measured by their ability to create anesthesia within the framework of the other desirable properties. The instant invention focuses on the dosage level where analgesia occurs but amnesia or lack of consciousness does not. In addition to identifying the dosage level where pain is sharply reduced or eliminated but awareness remains, a delivery system for safe and effective delivery of the agent is described.

82 Claims, 3 Drawing Sheets

U.S. PATENT DOCUMENTS

| | | | |
|---|---|---|---|
| 5,730,119 A * | 3/1998 | Lekholm | 128/200.24 |
| 5,771,882 A | 6/1998 | Psaros et al. | |
| 5,803,064 A * | 9/1998 | Phelps et al. | 128/203.12 |
| 6,029,664 A | 2/2000 | Zdrojkowski et al. | |
| 6,041,777 A | 3/2000 | Faithfulll et al. | |
| 6,131,571 A | 10/2000 | Lampotang et al. | |
| 6,216,690 B1 * | 4/2001 | Keitel et al. | 128/203.12 |
| 6,305,374 B1 * | 10/2001 | Zdrojkowski et al. | 128/204.21 |
| 6,443,150 B1 | 9/2002 | Pessala et al. | |
| 6,745,764 B2 | 6/2004 | Hickle | |
| 6,807,965 B1 * | 10/2004 | Hickle | 128/204.23 |

FOREIGN PATENT DOCUMENTS

| | | |
|---|---|---|
| EP | 0 911 052 | 4/1999 |
| HU | 192966 B | 8/1987 |
| JP | 2001-95921 | 4/2001 |
| WO | WO 99/62403 | 12/1999 |
| WO | WO 01/43803 | 6/2001 |

OTHER PUBLICATIONS

Bergsjø, P. et al. Comparison Between Nitrous Oxide and Methoxyflurane for Obstetrical Analgesia, Acta Obstet. Gynec. Scand., 1971, vol. 50, pp. 285-290.

Shnider, S.M. MD, et al. Report Abstracts, 36. Methoxyflurane in Obstetrics, Apr. 1969, vol. 33, No. 4, pp. 594-595.

Manohar, M, et al., Cerebral, renal, adrenal, intestinal, and pancreatic circulation in conscious ponies and during 1.0, 1.5, 2.0 minimal alveolar concentrations of haloethane-O2 anesthesia, American Journal of Veterinary Research, 1985, 46(12), pp. 2492-2497.

* cited by examiner

DRUG DELIVERY SYSTEM FOR CONSCIOUS SEDATION

CROSS REFERENCE TO A RELATED APPLICATION

Applicants hereby claim priority based on U.S. Provisional Patent Application No. 60/330,063, filed Oct. 17, 2001 entitled "Drug Delivery System for Conscious Sedation" which is incorporated herein by reference.

FIELD OF THE INVENTION

This invention relates to the field of analgesia and conscious sedation. More particularly, this invention provides an apparatus and method for the delivery of halogenated ethers for producing analgesia in a patient.

DISCUSSION OF RELATED ART

Since the mid-1800's conscious sedation/analgesia has been used in hospital and pre-hospital settings to relieve pain. Nitrous oxide (N2O) has been the primary inhalant agent in this regard. Sedative hypnotics such as diazepam and midazolam have been used as alternatives as have any number of barbitutes, opiods and agonist/antagonist agents.

Dentistry and oral surgery were the first applications of nitrous oxide conscious sedation and gained wide-spread acceptance following successful use on Queen Victoria. Subsequently, the use of conscious sedation spread throughout the hospital, to emergency rooms, in ambulances, and in other doctor offices.

Conscious sedation is a pain-blocking technique that allows a patient to remain partially alert during an invasive procedure. Analgesia is provided but, unlike anesthesia, the patient maintains awareness and recall. Specifically, the method is unique because patients do not perceive pain, but preserve their protective reflexes, maintain airways independently, and arouse in response to stimuli. Thus the risks of reduced or suppressed respiration associated with anesthesia are mitigated.

There are many benefits associated with conscious sedation. In particular, conscious sedation reduces anxiety in patients, particularly children. Accordingly, medical procedures are easier for the patient and the health care provider, as conscious sedation reduces patient tension and resistance to treatment. Furthermore, the technique has the potential for expansive applications. Studies have shown success with patient controlled analgesia.

The inhaled halogenated ethers offer a number of advantages in critical categories versus nitrous oxide conscious sedation or conscious sedation employing the sedative hypnotics. An example of some of the comparison with these agents is shown in Table 1.

TABLE 1

| | Sedative Hypnotics | | | |
|---|---|---|---|---|
| Features | Halogenated Ethers | Nitrous Oxide | IV Diazepam | IV Midazolam |
| Onset | Rapid | Rapid | Moderate | Moderate |
| Safety Profile | High | Teratogenic & Blood Disorders | Moderate | Moderate |
| Delivered with High $O_2$ Concentration | Yes | No | Optional | Optional |
| Abuse Potential | No | Recreational | Controlled Substance | Controlled Substance |
| Ease of Use & Reversal | Yes | Yes | Reversal Agent Required | Reversal Agent Required |
| Predictable Rapid Recovery to Street Ready | Yes | Yes | Reasonably Long Half-Life Rebound Possible | Reasonably Moderate Half-Life Rebound Possible |

The combination of these features makes the halogenated ethers attractive candidates for conscious sedation. However, there is also a need for a safe, accurate and cost effective delivery system.

The use of nitrous oxide based conscious sedation has declined in recent years principally reflecting the issues with the safety profile of the gas including those items listed above, but also because of its interference with methionine synthesis in prolonged exposure. These factors are particularly relevant to female health care professionals of childbearing age who face increased risk of spontaneous abortion due to nitrous oxide's teratogenetic profile.

$N_2O$ is relatively impotent. As discussed in the description of the invention below, this impotence requires that limits are placed on the inspired percentage of $N_2O$ to insure patients receive sufficient oxygen. The concentration of oxygen in the atmosphere approximates 21%. As a result, most international regulatory agencies, including the United States Food and Drug Administration ("FDA") established oxygen delivery guidelines to avoid hypoxia. The most common ratio is 70% $N_2O$/30% oxygen, although some delivery systems maintain 50% oxygen. At a 70% mixture of $N_2O$, conscious sedation occurs in most patients. The 70% $N_2O$/30% oxygen mixture, on a sustained basis at the delivery level has a Minimum Alveolar Content ("MAC") of 0.636 MAC.

Six inhaled ethers are in use today: halothane, methoxyflurane, enflurane, isoflurane, sevoflurane and desflurane. (Terrell, then of Airco, Inc., synthesized enflurane, isoflurane and desflurane.) These compounds were developed focusing on being non-flammable, non-addictive, potent, having rapid induction properties and cardiovascular stability. Traditionally these products have been packaged in 100 ml and 250 ml brown glass bottles and vaporized using an agent specific, temperature compensated system.

These drugs were developed for anesthesia. None of the inhaled ethers was developed as an inhalant analgesic. This reflected industry perceptions that either there was no need for an inhalant analgesic or there was the absence of cost-effective specialized equipment to administer these agents as analgesics. The equipment developed for anesthesia use in hospital settings was both sophisticated and expensive, frequently costing over $100,000. The combination of these factors virtually eliminated the ability to use these drugs as conscious sedation agents, particularly in the pre-hospital setting.

SUMMARY OF THE INVENTION

Inhalant anesthetics are developed with a number of properties including rapid onset and recovery, controllability, and, ideally, a broad safety profile. The efficacy of these agents is measured by their ability to create anesthesia (analgesia, amnesia, and loss of consciousness) within the framework of the other desirable properties. The instant invention focuses on the dosage level where analgesia occurs but amnesia or lack of consciousness does not. In addition to identifying the dosage level where pain is sharply reduced or eliminated but awareness remains, a delivery system for safe and effective delivery of the agent is described.

DETAILED DESCRIPTION OF THE INVENTION

Modern inhalation agents are halogenated ethers. They are generally characterized by a specific gravity between 1.0 and 2.0, low molecular weights (165.0-200.0), a low boiling point (22° C. to 104° C.), and significant potency—0.16%-7.8% of an agent on oxygen will put 99% of adults into anesthesia. These particular variables are important in the characterization of this invention as the drugs are converted from liquid to gas and delivered with a carrier gas—usually oxygen but sometimes a combination of oxygen and another gas or gases including oxygen, nitrous oxide and/or air.

However, the agents vary in many important respects. Some agents including methoxyflurane, halothane and sevoflurane are known to react to metals. To some extent these same agents decompose in the presence of "soda lime" (calcium hydroxide) and/or UV light. To a greater or lesser extent, all halogenated agents are solvents. A delivery system for conscious sedation must be compatible with the agent in use.

EXAMPLE I

The potency of anesthetic agents is measured by the minimum alveolar concentration of an anesthetic producing immobility in 50% of patients, defined as 39 year old males, undergoing surgical incision ("MAC"). The MAC of potent inhaled agents varies significantly. The MAC of nitrous oxide, the leading inhalant conscious sedation drug, can only be determined under unusual conditions of temperature and pressure, such as a hyper baric chamber, when additional dosages can be provided without creating hypoxia. Research suggests the MAC of nitrous oxide to be 110%. Thus, to create anesthesia, most patients would suffocate. Conversely, the MAC of methoxyflurane, an early-halogenated ether is only 0.16%. In present inhalant conscious sedation systems, nitrous oxide is delivered in conjunction with a minimum of 30% oxygen to insure the patient maintains a sufficient level of oxygen. In the United States, the Food and Drug Administration ("FDA") has set 70% nitrous oxide as the limit for delivery in a conscious sedation unit. For this description a MAC equivalent of 70% nitrous oxide will be used for comparison with other inhalants, as shown in Table 2.

TABLE 2

| Drug | MAC* | Implied CS Level | MAC Equivalent | Inhaled Oxygen |
|---|---|---|---|---|
| Nitrous Oxide | 110.00% | 70.00% | .636 | 30.00% |
| Existing Inhalation Drugs | | | | |
| Methoxyflurane | 0.16% | 0.11% | | 99.89% |
| Halothane | 0.75% | 0.48% | | 99.52% |
| Isoflurane | 1.15% | 0.73% | | 99.27% |
| Enflurane | 1.68% | 1.07% | | 98.93% |
| Sevoflurane | 2.00% | 1.27% | | 98.73% |
| Desflurane | 6.00% | 3.82% | | 96.18% |

*MAC is shown in 100% oxygen for middle-aged men. MAC varies with age and personal habits including alcohol and drug ingestion.

For patients who would benefit from higher levels of oxygen delivery including, but not limited to, those with Coronary Artery Disease (CAD), replacement of nitrous oxide with an inhalant analgesia could provide improvement in myocardial oxygenation.

EXAMPLE II

Figure 1:
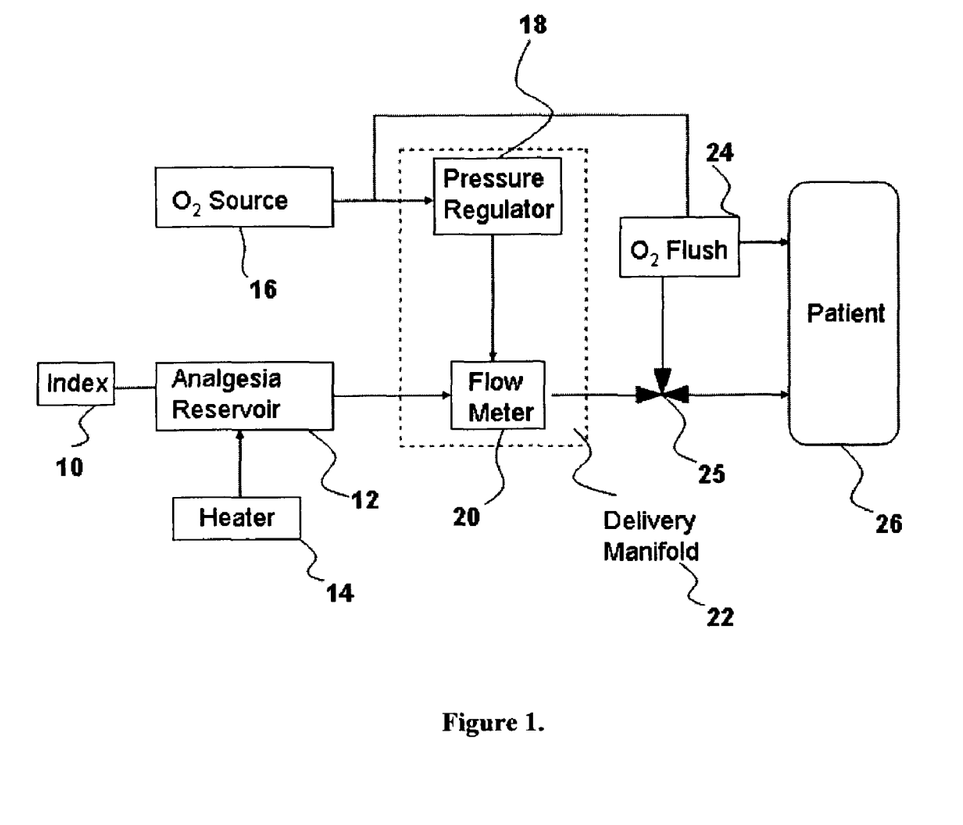
FIG. 1 is a block diagram showing an embodiment of the invention.

To deliver a concentration of the relevant agent that creates analgesia but not loss of awareness (either amnesia or loss of consciousness) requires a finely calibrated instrument through which the agent can flow with very minimal risk of overdose or delivery of hypoxic mixture (FIG. 1.) To be practical in the outpatient setting the device must be cost-effective, preferably costing less than anesthesia machines which presently cost $100,000 or more. Compared to the sedative hypnotics, barbitutes, opoids and agonist/antagonists that can also be used of sedation, the invention offers more rapid onset and recovery and less risk of abuse potential. The invention therefore comprises an oxygen delivery mechanism, either an $O_2$ cylinder(s) and/or manifold system to oxygen storage ("$O_2$ source") 16 and a reservoir for the analgesia agent 12, for example but not limited to an agent compatible cylinder; a heating element 14 attached to the analgesia reservoir 12, for example but not limited to a heating plate, linked to an ambient temperature sensor to allow compensation for environmental temperature and pressure. Heating of the analgesia reservoir 12 by the heating element 14 allows control of the pressure of the agent in the reservoir such that the flow of the agent can be properly regulated despite changing ambient temperatures. The reservoir system comprises a mated index system 10 to insure that only the agent specified can be filled into the reservoir and, once filled, can only be mated to a delivery system specific to that agent. Oxygen from the $O_2$ source 16 flows through a delivery manifold system 22 including a sensitive pressure regulator 18 to a flow meter 20, either analog or electronic, where it is mixed in strict proportions with the agent from the reservoir 12 and will accurately meter the dosage of the agent to +/−0.1% of gas flow or less. While the agent could be routed to the flow meter 20 directly, it may be also be arranged to flow through the delivery manifold 22 to regulate flow and insure that safety devices including but not limited to an automatic agent shutoff system if oxygen flow is shutoff or determined to be insufficient. An oxygen flush system 24 allows the practitioner to rapidly fill a patient's lungs and force exhalation of the residual agent. The system is arranged so that when the $O_2$ flush 24 is triggered the flow of analgesic is automatically ceased because the $O_2$ flush 24 is linked to the analgesia reservoir 12 by a three-way valve 25 such that when the $O_2$ flush 24 is on the analgesic 12 is off, and vice versa. The mixing head and/or flow meter system allows the user to regulate gas flow and agent concentration up to the conscious sedation limits established by the appropriate regulatory authority, and is sufficiently accurate in calibration to allow agent flow to approach the desired CS levels. In addition, the controlled heating element 14 and the flow meter 20 can be operated in a co-operative relationship to regulate the flow of the analgesic agent.

Figure 2:
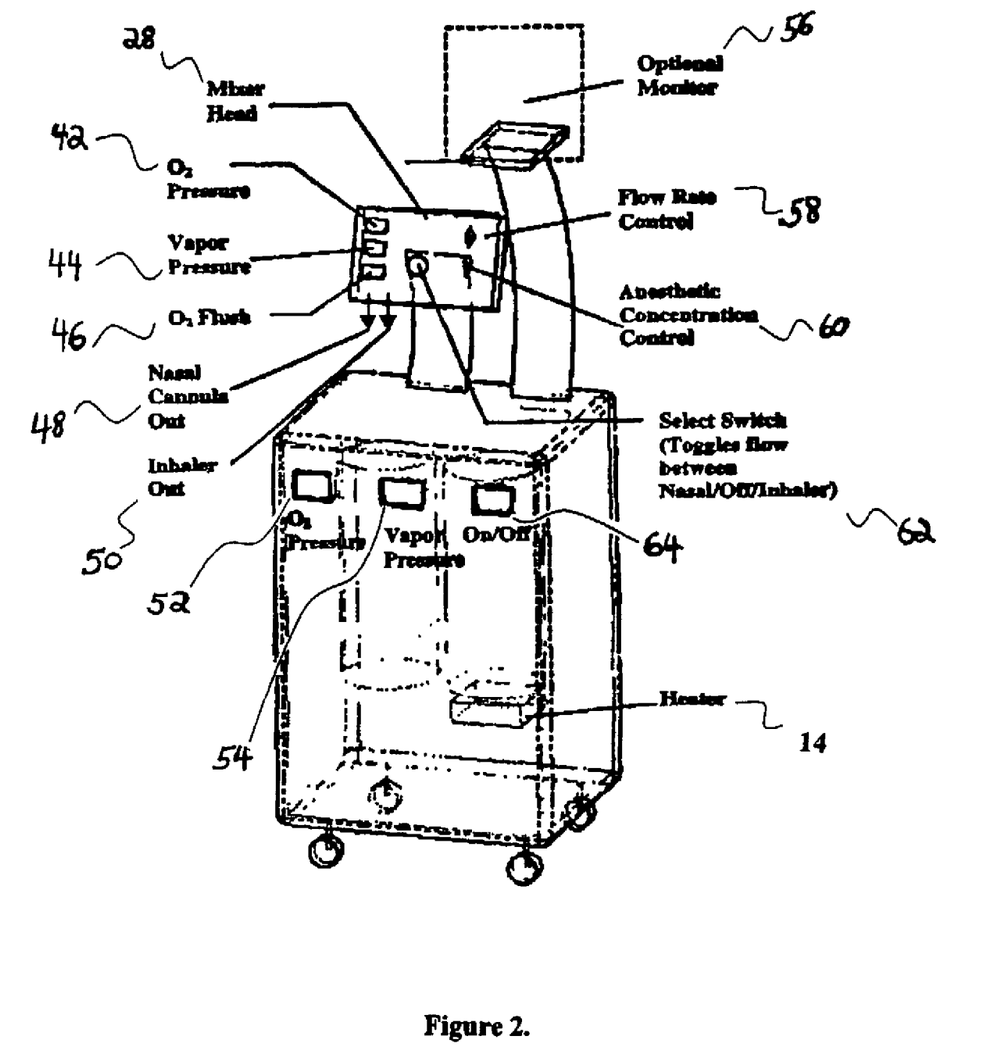
FIG. 2 is a diagrammatic perspective view of another embodiment of the invention.
Figure 3:
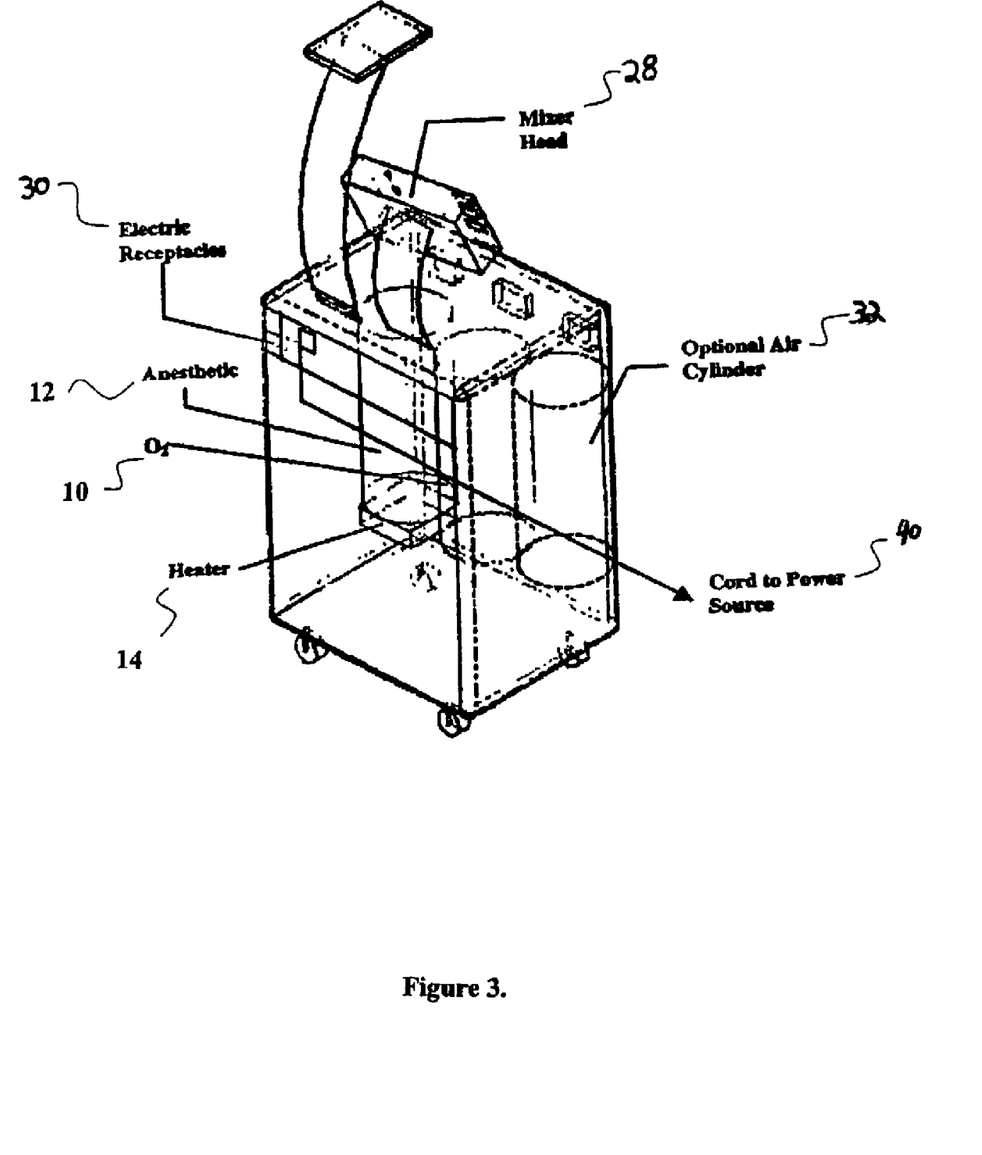
FIG. 3 is a diagrammatic perspective view similar to FIG. 2 but rotated about 180°.

As shown in FIGS. 2 and 3, an embodiment of the invention is a stand alone doctor's office unit. FIG. 2 shows a heater 14; mixer head 28; an oxygen pressure control 42; a vapor pressure control 44; an oxygen flush control 46; a nasal cannula out port 48; an inhaler out port 50; an oxygen pressure gauge 52; a vapor pressure gauge 54; an optional monitor 56; a flow rate control 58; an anesthetic concentration control 60; a select nasal/off/inhaler switch 62; and an on/off control 64.

FIG. 3 shows an oxygen source 10; an anesthetic source 12; a heater 14; a mixer head 28; electric receptacles 30; an optional air cylinder 32; and a power cord 40. These features may be coupled with others including but not limited to the ability to modify the unit to be portable for emergency or military use; the ability to modify the unit for patient controlled analgesia ("PCA"); attaching a scavenging system for recovering exhaled agent and removing it from the environment; incorporating or allowing the unit to be compatible with physiologic monitoring including but not limited to oximetry, EKG, blood pressure, carbon dioxide monitoring and depth of consciousness monitors; the ability in one or more configurations to make the device compatible with diagnostic imaging devices including but not limited to nuclear magnetic resonance devices (MRI's) to allow analgesic delivery to patients requiring sedation or pain relief during MRI imaging.

Clinical utilization of conscious sedation system is possible in a wide ranging number of procedures including but not limited to dental and oral surgery procedures, burn debridment, pain relief in emergency and trauma situations, administration in the intensive care, cardiac care or critical care units, in examination or work on the extremities including podiatric procedures, labor and delivery, to reduce anxiety in individuals with fear of needle insertion, and where prolonged immobilization would be difficult without the delivery of a sedation agent.

Additionally, the invention has the following attributes. The invention increases oxygenation of blood, an important feature for individuals with poor myocardial or cerebral oxygenation. The invention increases occupational safety when analgesics described herein are substituted for nitrous oxide, an important feature for women of child-bearing age. The invention can reduce claustrophobia-associated anxiety and relieve pain in patients facing prolonged periods of inactivity, such as during nuclear magnetic resonance imaging (MRI) when used with an MR-safe (1.5 tesla) version of the delivery system. Similarly, the invention may be used for sedation in Intensive Care Units (ICU), Critical Care Units (CCU), or during cardiac catheterization, implantable defibrillator or pacemaker adjustments, and in general pain relief. The device may be provided in alternative configurations, such as with a stand or method for holding patient monitors, including integration of the monitors with the system. Additionally, the device may be provided with a regulator system that senses the depth of a patient's inhalation to allow safe patient controlled analgesia administration.

Although embodiments of the invention have been described herein, the invention is not limited to such embodiments. The claims that follow are directed to the invention, and are intended to describe the invention, but their literal language is not intended to limit the scope of the invention.

We claim:

1. A method for delivery of a mixture to a patient effective to produce analgesia without loss of consciousness in a patient wherein the method comprises:
   forming a gaseous mixture of oxygen and a halogenated material selected from the group consisting of halogenated ethers and halothane by mixing oxygen with the halogenated material in a delivery manifold, the manifold having a controller configured to provide a gas having a concentration of the halogenated material that is limited to not more than about 0.636 MAC; and
   b) controlling the proportions of oxygen and halogenated material in the gaseous mixture by metering a liquid flow of the halogenated material into a gas containing the oxygen such that the gaseous mixture comprises a ratio of oxygen to halogenated material effective for producing analgesia without loss of consciousness in the patient;
   c) delivering said gaseous mixture to the patient to produce analgesia without loss of consciousness in the patient; and
   d) performing a medical or dental intervention or procedure during analgesia while the patient is conscious.

2. The method of claim 1 wherein the halogenated material is enflurane.

3. The method of claim 1 wherein the halogenated material is isoflurane.

4. The method of claim 1 wherein the halogenated material is sevoflurane.

5. The method of claim 1 wherein the halogenated material is desflurane.

6. A system for delivering gas to a patient to produce analgesia without loss of consciousness in the patient comprising:
   a) an oxygen source;
   b) a reservoir suitable for storing a liquid phase of an analgesia producing agent, the agent being a halogenated material selected from the group consisting of halogenated ethers and halothane;
   a delivery manifold having a pair of inputs connected to the oxygen source and to the reservoir, respectively, and having an output, the manifold providing a gaseous mixture of oxygen and the analgesia producing agent by metering a flow of the liquid halogenated material into the oxygen, the manifold having a controller configured to provide the gaseous mixture such that the halogenated material is limited to not more than about 0.636 MAC for producing analgesia without loss of consciousness; and
   d) means for conveying the gaseous mixture from the output of the delivery manifold to a patient for producing analgesia without loss of consciousness in the patient while a medical or dental intervention or procedure is carried out.

7. The gas delivery system of claim 6, wherein the delivery manifold comprises a pressure regulator and a flow meter connected in fluid communication, the flow meter being in fluid communication with the output of the delivery manifold.

8. The gas delivery system of claim 7, wherein the pressure regulator is in fluid communication with the input of the delivery manifold connected to the oxygen source and the flow meter is in fluid communication with the input of the delivery manifold connected to the reservoir.

9. The gas delivery system of claim 6, further including heating means operatively associated with the reservoir containing analgesia producing agent and ambient temperature sensing means in controlling relation to a heating means to provide compensation for changes in environmental temperature conditions.

10. The gas delivery system of claim 6, further including an oxygen flush arrangement operatively coupled between the oxygen source and a patient.

11. The gas delivery system of claim 6 wherein the oxygen source comprises a cylinder.

12. The gas delivery system of claim 6 wherein the reservoir comprises a cylinder.

13. The gas delivery system of claim 6 wherein the reservoir has a mated index.

14. The gas delivery system of claim 6 wherein the pressure regulator is digital.

15. The gas delivery system of claim 6 wherein the pressure regulator is analog.

16. The gas delivery system of claim 6 wherein a gas scavenging system is provided.

17. A drug delivery system having a reservoir to provide halogenated material, the halogenated material being selected from the group consisting of halogenated ethers and halothane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC for producing analgesia without loss of consciousness in a patient that is undergoing a medical or dental intervention or procedure.

18. The drug delivery system of claim 17, wherein the halogenated material is halothane.

19. The drug delivery system of claim 17, wherein the halogenated material is enflurane.

20. The drug delivery system of claim 17, wherein the halogenated material is isoflurane.

21. The drug delivery system of claim 17, wherein the halogenated material is sevoflurane.

22. The drug delivery system of claim 17, wherein the halogenated material is desflurane.

23. A drug delivery system according to claim 17 in a configuration selected from the group consisting of a portable version for military use, a wall mounted configuration, an office cabinetry configuration and a version as part of a gas delivery system.

24. A drug delivery system according to claim 23 with scavenging of exhaled patient gases.

25. A drug delivery system according to claim 23 without scavenging of exhaled patient gases.

26. A drug delivery system according to claim 17 or 23 operatively associated with means for holding patient monitors selected from the group consisting of devices for oxygen monitoring, oximetry, EKG monitoring, blood pressure monitoring, carbon dioxide monitoring and depth of consciousness monitoring.

27. A drug delivery system according to claim 17 or 23 integrated with patient monitors selected from the group consisting of oxygen monitoring, oximetry, EKG monitoring, blood pressure monitoring, carbon dioxide monitoring and depth of consciousness monitoring.

28. A drug delivery system according to claim 17 or 23 further including a regulator system to sense depth of patient inhalation measured in units selected from the group consisting of pressure per square inch (PSI) and millimeters of mercury.

29. A drug delivery system according to claim 17 with scavenging of exhaled patient gases.

30. A drug delivery system according to claim 17 without scavenging of exhaled patient gases.

31. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC and having a delivered oxygen concentration effective for use with patients having poor myocardial or cerebral oxygenation or coronary artery disease and to produce analgesia without loss of consciousness in a patient that is undergoing a medical or dental intervention or procedure during analgesia while the patient is conscious.

32. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC and featuring an absence of nitrous oxide so as to provide increased occupational safety particularly among women of child bearing age and/or persons addicted to nitrous oxide and to produce analgesia without loss of consciousness in a patient that is undergoing a medical or dental intervention or procedure analgesia while the patient is conscious.

33. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC and having MR-safety (1.5 tesla) so as to reduce anxiety in a patient related to a medical or dental procedure, claustrophobia or mental incapacitation and so as to produce analgesia without loss of consciousness in the patient facing prolonged periods of inactivity such as during nuclear magnetic resonance (MRI), wherein the patient is undergoing the procedure during analgesia while the patient is conscious.

34. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC and is in operative relationship with an intensive care unit (ICU), critical care unit (CCU) or cardiac catheterization laboratory in conjunction with situations such as prolonged intubation and depth of consciousness measurement and patient interventions such as dressing changes and implantable cardiac defibrillator or pacemaker adjustment and general pain relief to produce analgesia without loss of consciousness in a patient that is undergoing a medical or dental intervention or procedure during analgesia while the patient is conscious.

35. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC to produce analgesia without loss of consciousness in a patient and operating with scavenging of exhaled patient gases wherein the patient is undergoing a medical or dental intervention or procedure during analgesia while the patient is conscious.

36. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC to produce analgesia without loss of consciousness in a patient and operating without scavenging of exhaled patient gases wherein the patient is undergoing a medical or dental intervention or procedure during analgesia while the patient is conscious.

37. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC for producing analgesia without loss of consciousness in a patient, and further including a regulator system to sense depth of patient inhalation measured in units selected from the group consisting of pressure per square inch (PSI) and millimeters of mercury while producing analgesia without loss of consciousness in a patient that is undergoing a medical or dental intervention or procedure during analgesia while the patient is conscious.

38. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of the halogenated material that is limited to not more than about 0.636 MAC for producing analgesia without loss of consciousness in a patient and having an absence of nitrous oxide so as to provide increased occupational safety particularly among women of child bearing age and/or persons addicted to nitrous oxide while producing analgesia without loss of consciousness in a patient that is undergoing a medical or dental intervention or procedure.

39. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide the gaseous mixture having a concentration of halogenated agent that is limited to not more than about 0.636 MAC for producing analgesia without loss of consciousness in a patient that is undergoing a medical or dental intervention or procedure during analgesia while the patient is conscious, and having an increased delivered oxygen concentration for use with patients having poor myocardial or cerebral oxygenation or coronary artery disease.

40. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide the gaseous mixture having a concentration of halogenated agent that is limited to not more than about 0.636 MAC for producing analgesia without loss of consciousness in a patient undergoing a medical or dental intervention or procedure and having an absence of nitrous oxide so as to provide increased occupational safety particularly among women of child bearing age and/or persons addicted to nitrous oxide while producing analgesia without loss of consciousness in a patient that is undergoing a medical or dental intervention or procedure during analgesia while the patient is conscious.

41. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide the gaseous mixture having a concentration of halogenated agent that is limited to not more than about 0.636 MAC for producing analgesia without loss of consciousness in a patient and having MR-safety (1.5 tesla) so as to reduce anxiety related to procedure, claustrophobia or mental incapacitation and so as to provide analgesia without loss of consciousness to patients facing prolonged periods of inactivity such as during nuclear magnetic resonance (MRI) wherein the patient is undergoing a medical or dental intervention or procedure during analgesia while the patient is conscious.

42. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide the gaseous mixture having a concentration of halogenated agent that is limited to not more than about 0.636 MAC and for producing analgesia without loss of consciousness in a patient that is undergoing a medical or dental intervention or procedure during analgesia while the patient is conscious, and in operative relationship with intensive care unit (ICU), critical care unit (CCU) or cardiac catheterization laboratory in conjunction with situations such as prolonged intubation and depth of consciousness measurement and patient interventions such as dressing changes and implantable cardiac defibrillator or pacemaker adjustment and general pain relief.

43. A method for delivery of a mixture of gases to a patient effective to produce a sedative state without loss of consciousness in a patient wherein the method comprises:
   a) forming a gaseous mixture of oxygen and halogenated material selected from the group consisting of halogenated ethers and halothane by mixing oxygen with halogenated material;
   b) controlling the proportions of oxygen and halogenated material in the gaseous mixture with a delivery manifold having a controller configured to provide the gaseous mixture, which comprises a ratio of oxygen to halogenated material in a concentration that is limited to not more than about 0.636 MAC and is effective for producing the sedative state without loss of consciousness in the patient wherein the halogenated material is stored in a liquid phase in a reservoir and a flow of the liquid halogenated material is metered into the oxygen to form the gaseous mixture; and
   c) delivering said gaseous mixture to the patient to produce the sedative state without loss of consciousness in the patient that is undergoing a medical or dental intervention or procedure during the sedative state while the patient is conscious.

44. The method of claim 43 wherein the halogenated material is halothane.

45. The method of claim 43 wherein the halogenated material is enflurane.

46. The method of claim 43 wherein the halogenated material is isoflurane.

47. The method of claim 43 wherein the halogenated material is sevoflurane.

48. The method of claim 43 wherein the halogenated material is desflurane.

49. A system for delivering gas to a patient to produce a sedative state without loss of consciousness in the patient comprising:
   a) an oxygen source;
   b) a reservoir containing a liquid-phase sedation-producing agent in the form of halogenated material selected from the group consisting of halogenated ethers and halothane;
   c) a delivery manifold having a pair of inputs connected to the oxygen source and to the reservoir, respectively, and having an output, the manifold providing a gaseous mixture of oxygen and halogenated material by metering a flow of the liquid halogenated material into the oxygen, the manifold having a controller configured to provide a concentration of the halogenated material that is limited to not more than about 0.636 MAC for producing the sedative state without loss of consciousness such that the gaseous mixture comprises a ratio of oxygen to halogenated material effective for producing the sedative state without loss of consciousness in a patient; and
   d) means for conveying the gaseous mixture from the output of the delivery manifold to a patient for producing the sedative state without loss of consciousness in a patient that is undergoing a medical or dental intervention or procedure during the sedative state while the patient is conscious.

50. The gas delivery system of claim 49, wherein the delivery manifold comprises a pressure regulator and a flow meter connected in fluid communication, the flow meter being in fluid communication with the output of the delivery manifold.

51. The gas delivery system of claim 50, wherein the pressure regulator is in fluid communication with the input of the delivery manifold connected to the oxygen source and the flow meter is in fluid communication with the input of the delivery manifold connected to the reservoir containing a halogenated material producing sedation without loss of consciousness.

52. The gas delivery system of claim 49, further including heating means operatively associated with the reservoir containing sedation producing agent and ambient temperature sensing means in controlling relation to the heating means to provide compensation for changes in environmental temperature conditions.

53. The gas delivery system of claim 49, further including an oxygen flush arrangement operatively coupled between the oxygen source and a patient.

54. The gas delivery system of claim 49, wherein the oxygen source comprises a cylinder.

55. The gas delivery system of claim 49, wherein the halogenated material reservoir comprises a cylinder.

56. The gas delivery system of claim 49, wherein the halogenated material reservoir has a mated index.

57. The gas delivery system of claim 49, wherein the pressure regulator is digital.

58. The gas delivery system of claim 49, wherein the pressure regulator is analog.

59. The gas delivery system of claim 49, wherein a gas scavenging system is provided.

60. A drug delivery system having a reservoir to provide halogenated material, the halogenated material being selected from the group consisting of halogenated ethers and halothane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC for producing a sedative state without loss of consciousness in a patient that is undergoing a medical or dental intervention or procedure during the sedative state while the patient is conscious.

61. The use of halothane in the delivery system of claim 60 as an inhaled analgesic for producing sedation without loss of consciousness in a patient.

62. The use of enflurane in the delivery system of claim 60 as an inhaled analgesic for producing sedation without loss of consciousness in a patient.

63. The use of isoflurane in the delivery system of claim 60 as an inhaled analgesic for producing sedation without loss of consciousness in a patient.

64. The use of sevoflurane in the delivery system of claim 60 as an inhaled analgesic for producing sedation without loss of consciousness in a patient.

65. The use of desflurane in the delivery system of claim 60 as an inhaled analgesic for producing sedation without loss of consciousness in a patient.

66. A drug delivery system according to claim 60 in a configuration selected from the group consisting of a portable version for military use, a wall mounted configuration, an office cabinetry configuration and a version as part of a gas delivery system.

67. A drug delivery system according to claim 66 with scavenging of exhaled patient gases.

68. A drug delivery system according to claim 66 without scavenging of exhaled patient gases.

69. A drug delivery system according to claim 60 or 66 operatively associated with means for holding patient monitors selected from the group consisting of devices for oxygen monitoring, oximetry, EKG monitoring, blood pressure monitoring, carbon dioxide monitoring and depth of consciousness monitoring.

70. A drug delivery system according to claim 60 or 66 integrated with patient monitors selected from the group consisting of devices for oxygen monitoring, oximetry, EKG monitoring, blood pressure monitoring, carbon dioxide monitoring and depth of consciousness monitoring.

71. A drug delivery system according to claim 60 or 66 further including a regulator system to sense depth of patient inhalation measured in units selected from the group consisting of pressure per square inch (PSI) and millimeters of mercury.

72. A drug delivery system according to claim 60 with scavenging of exhaled patient gases.

73. A drug delivery system according to claim 60 without scavenging of exhaled patient gases.

74. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a gaseous concentration of halogenated material that is limited to not more than about 0.636 MAC and having MR-safety (1.5 tesla) so as to reduce anxiety related to procedure, claustrophobia or mental incapacitation and so as to produce a sedative state without loss of consciousness in patients facing prolonged periods of inactivity such as during nuclear magnetic resonance imaging (MRI) wherein the patient is undergoing a medical or dental intervention or procedure during the sedative state while the patient is conscious.

75. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC to produce a sedative state without consciousness in a patient that is undergoing a medical or dental intervention or procedure during the sedative state while the patient is conscious, and operating with scavenging of exhaled patient gases.

76. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC to produce a sedative state without loss of consciousness in a patient that is undergoing a medical or dental intervention or procedure during the sedative state while the patient is conscious, and operating without scavenging of exhaled patient gases.

77. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC for producing a sedative state without loss of consciousness in a patient and further including a regulator system to sense depth of patient inhalation measured in units selected from the group consisting of pressure per square inch (PSI) and millimeters of mercury while producing sedation without loss of consciousness in a patient that is undergoing a medical or dental intervention or procedure during the sedative state while the patient is conscious.

78. A drug delivery system having a reservoir to provide halogenated material, the halogenated material being selected from the group consisting of halothane, enflurane, isoflurane, sevoflurane and desflurane, wherein the reservoir is suitable for storing the halogenated material in a liquid phase, and a delivery manifold for providing a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC for producing a sedative state without loss of consciousness in a patient and having an absence of nitrous oxide so as to provide increased occupational safety particularly among women of child bearing age and/or persons addicted to nitrous oxide while producing sedation without loss of consciousness in a patient that is undergoing a medical or dental intervention or procedure during the sedative state while the patient is conscious.

79. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide a gaseous concentration of halogenated material that is limited to not more than about 0.636 MAC for producing a sedative state without loss of consciousness in a patient that is undergoing a medical or dental intervention or procedure during the sedative state while the patient is conscious, and having an increased delivered oxygen concentration for use with patients having poor myocardial or cerebral oxygenation or coronary artery disease.

80. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide a concentration of the halogenated material in a gas phase that is limited to not more than about 0.636 MAC for producing a sedative state without loss of consciousness in a patient and having an absence of nitrous oxide so as to provide increased occupational safety particularly among women of child bearing age and/or persons addicted to nitrous oxide while producing sedation without loss of consciousness in a patient that is undergoing a medical or dental intervention or procedure during the sedative state while the patient is conscious.

81. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide a gaseous concentration of halogenated material that is limited to not more than about 0.636 MAC for producing a sedative state without loss of consciousness in a patient and having MR-safety (1.5 tesla) so as to reduce anxiety related to procedure, claustrophobia or mental incapacitation and so as to provide sedation without loss of consciousness to patients facing prolonged periods of inactivity such as during nuclear magnetic resonance (MRI) wherein the patient is undergoing a medical or dental intervention or procedure during the sedative state while the patient is conscious.

82. A therapeutic drug delivery method utilizing halogenated material selected from the group consisting of halothane, enflurane, isoflurane, sevoflurane and desflurane, wherein a reservoir stores the halogenated material in a liquid phase, and wherein a delivery manifold provides a gaseous mixture of oxygen and the halogenated material by metering a flow of the liquid halogenated material into the oxygen, the manifold including a controller configured to provide a gaseous concentration of halogenated material that is limited to not more than about 0.636 MAC for producing a sedative state without loss of consciousness in a patient that is undergoing a medical or dental intervention or procedure during the sedative state while the patient is conscious, and in operative relationship with intensive care unit (ICU), critical care unit (CCU) or cardiac catheterization laboratory in conjunction with situations such as prolonged intubation and depth of consciousness measurement and patient interventions such as dressing changes and implantable cardiac defibrillator or pacemaker adjustment and general pain relief.

* * * * *